United States Patent [19]

Carabasi et al.

[11] Patent Number: 4,883,755

[45] Date of Patent: Nov. 28, 1989

[54] METHOD OF REENDOTHELIALIZING VASCULAR LININGS

[75] Inventors: R. Anthony Carabasi, Bryn Mawr; Bruce E. Jarrell, Philadelphia, both of Pa.; Stuart K. Williams, Wilmington, Del.

[73] Assignee: Thomas Jefferson University, Philadelphia, Pa.

[21] Appl. No.: 114,242

[22] Filed: Oct. 28, 1987

[51] Int. Cl.$^4$ .................. C12N 5/00; A01N 1/00; A61K 35/14; A61K 37/00

[52] U.S. Cl. .................. 435/240.2; 435/1; 435/2; 424/77; 424/407; 514/2; 514/802; 604/4

[58] Field of Search ............ 435/240.2, 240.25, 240.1, 435/1, 2; 424/77, 407; 514/2, 802; 604/4

[56] References Cited

PUBLICATIONS

Williams S. "Isolation and Culture of Microvessel and Large-Vessel Endothelial Cells: Their Use in Transport and Clinical Studies" in *Micro Vascular Perfusion and Transport in Health and Disease*, eds. McDonagh. Karger Publishers, Switzerland Jan. 1987, pp. 204–243.
Jarrell et al *JVS* 1984, 1: 757–764, "Human Adult Endothelial Cell Growth in Culture".
Steele, P., et al., *Circ. Res.*, 57, No. 1:105–112 (1985).
Osterud, B., et al., *J. Proc. Natl. Acad. Sci. U.S.A.*, 74, p. 5260 (1977).
Harker, L., et al., *J. Clin. Invest.*, 58, 731 (1976).
Friedman, R., et al., *J. Clin. Invest.*, 60, 1191 (1977).
Goldberg, J. D., et al., *J. Science*, 209, 611 (1980).
Gimbrone, M. A., Jr., in: Jafe, E. A., Ed., *Biology of Endothelial Cells*, Marinus Nijhoff Publishers, pp. 97–107 (1984).
Hoff, H., *Thromb. Haemostas.*, 40, 121 (1970).
Jaffe, E. A., et al., *J. Clin. Invest.*, 52:2745 (1973).
Maciag, T., et al., *J. Cell Biol.*, 91:420 (1981).
Thornton, S. C., et al., *Science*, 222:623–624 (1983).
Jarrell, B. E., et al., *Surgery*, vol. 100, No. 2, pp. 392–399 (Aug. 1986).
Watkins, M. T., et al., *J. Surg. Res.*, 36:588–596 (1984).
Williams, S. K., et al., *J. Surg. Res.*, 38:618–629 (1985).
Baker, K. S., et al., *Am. J. Surg.*, 150:197–200 (1985).
Jarrell, B. E., et al., *Ann. Surg.*, vol. 203, No. 6, pp. 671–678 (Jun. 1986).
Radomski, J., et al., *J. Surg. Res.*, 42, 133–140 (1987).
Bush, Jr., Harry L., et al., *Journal of Vascular Surgery*, vol. 3, No. 1, pp. 118–125 (Jan. 1987).
Burkel. W. E., "The Development of Cellular Linings in Artificial Vascular Prostheses", appearing in *Biocompatible Polymers, Metals, and Composites*, ed. by M. Szycher, 1983.
Belden, T. A., et al., "Endothelial Cell Seeding of Small-Diameter Vascular Grafts", *Transactions American Society for Artificial Internal Organs*, vol 28 (Apr. 14–16), pp. 173–184 (1982).
Dilley, et al., "Endothelial Seeding of Fascular Prostheses", Jaffe ed. *Biology of Endothelial Cells*, the Hague: Martinus Nijhoff, 1984, pp. 401–411.
Stanley, et al., "Enhanced Patency of Small Diameter Externally Supported Dacron Iliofemoral Grafts Seeded with Endothelial Cells", *Surgery*, 92:994–1005 (1982).
Williams, "Vesicular Transport of Proteins by Capillary Endothelium", *Annals of the New York Academy of Sciences*, 457–467 (1983).
Kern, et al., "Isolation and Culture of Microvascular Endothelium from Human Adipose Tissue", *J. Clin. Invest.*, 71:1822–1829 (Jun., 1983).

Primary Examiner—Charles F. Warren
Assistant Examiner—Lori Y. Beardell
Attorney, Agent, or Firm—Woodcock Washburn Kurtz Mackiewicz & Norris

[57] ABSTRACT

A method for treating the vascular passage of a patient, damaged by procedures such as an endarterectomy which denude portions of the vascular passages of their endothelial cell linings, is disclosed. In this method, endothelial cells are isolated from the patient's own microvessels, the flow of blood through the patient's damaged vascular passage is interrupted, the endothelial cells isolated from the patient's microvessels are applied to the surface of the denuded portion of the patient's vascular passage in a density sufficient to provide covereage of at least about 50% of said denuded portion, and interruption of blood flow through the vascular passage is maintained for a period of time sufficient to allow the sodded cells to form an attachment to the vascular lining sufficient to withstand the shear created by resumed blood flow through the vascular passage.

13 Claims, No Drawings

METHOD OF REENDOTHELIALIZING VASCULAR LININGS

BACKGROUND OF THE INVENTION

1. Field of the Invention

This invention relates to a method of reendothelializing the vascular passage of a patient, the lining of which has been substantially denuded of endothelial cells by virtue, for example, of procedures such as endarterectomy.

2. Related Applications

U.S. Ser. No. 742,086, filed June 6, 1985, by Williams and Jarrell, discloses a method for treating a synthetic or naturally occurring implant intended for implantation in a human patient comprising the steps of obtaining human microvascular endothelial cell rich tissue from that patient, separating microvascular endothelial cells from that tissue; and applying said microvascular endothelial cells onto said implant to provide at least about 50% or greater confluence of said cells on the surface of said implant to be treated.

U.S. Ser. No. 848,453, filed on Apr. 4, 1986 as a continuation-in-part of U.S. Ser. No. 742,086, discloses a method of treating an implant intended for implantation in a human patient, comprising the steps of providing a synthetic substrate material and treating that material with Type IV/V collagen to improve human endothelial cell adhesion, proliferation and morphology. In the preferred embodiment, the endothelial cells are derived from the endothelial cell rich tissue of the patient undergoing implantation.

U.S. Ser. No. 927,745, filed by Jarrell and Williams on Nov. 6, 1986, discloses a method of determining endothelial cell coverage on a prosthetic surface.

The disclosures of these three applications are hereby incorporated by reference.

3. Description of the Art

Atherosclerotic vascular disease remains the leading cause of death among Americans. As medical science has become more sophisticated, increasing use of invasive vascular procedures are being applied to obstructed vessels in the absence of effective preventive or therapeutic drug modalities. For example, the use of arterial endarterectomy as well as percutaneous balloon dilatation of vessels for pathologic stenosis have become routine hospital procedures. Although these and other procedures are often successful, a common complication after the procedures is the occurrence of vessel wall abnormalities. These abnormalities include recurrent stenosis due to atherosclerosis, smooth muscle proliferation, loss of vessel wall integrity as a result of fibrosis and thrombosis of the vessel. Injury to or removal of the endothelial cells lining the blood vessels is one of several common denominators inherent to vascular procedures, and current data suggest that spontaneous reendothelialization of these injuries may occur slowly, partially, or not at all.

The endothelial lining of blood vessels is a highly complex, multi-functional cell surface. These cells interact with both the blood and the underlying vessel wall components to maintain a physiological homeostasis. The effects of endothelial injury have been studied in several experimental models mostly designed to study the development of biological mechanisms. After endothelial injury, the vessel wall loses its non-thrombogenic properties. One of the first events to occur is platelet adherence to the vessel surface, which is extensive over the first several days but diminishes over the following week. Steele, P., Chesebro, J., Stanson, A., Holmes, D., Dewanjee, M., Badimon, L., Fuster, V., *Circ. Res.* 57, No. 1:105–112 (1985). Platelets adhere to the subendothelium and undergo a release reaction, inducing further activation of the plasma coagulation system. Osterud, B. et al., *J. Proc. Natl. Acad. Sci. U.S.A.*, 74, p. 5260 (977). One of the released products is platelet derived growth factor (PDGF), which is mitogenic for vascular smooth muscle cells grown in tissue culture. It has been postulated that local release of this factor may play a role in the genesis of intimal hyperplasia and atherosclerosis. Harker, L. et al., *J. Clin. Invest.*, 58, 731 (1976); Friedman, R. et al., *J. Clin. Invest.* 60, 1191 (1977). Other substances released from platelets include heparitinase and platelet factor 4. The latter protein has high affinity for heparin and has been shown to penetrate into the vascular media after de-endothelialization. Goldgerg, J. D. et al., *J. Science.* 209, 611 (1980). Macrophages, which are also a rich source of SMC mitogens, are frequently present in the injured area. Gimbrone, M. A. Jr., In: Jaffe, E. A., Editor, *Biology of Endothelial Cells*, Martinus Nijhoff Publishers, pp. 97–107 (1984). The final response of the injured arterial wall, independent of whether the injury is chemical, mechanical or biological, is characterized by proliferation of cells in the intima to form a fibro-musculo-elastic plaque. Hoff, H., *Thromb. Haemostas.*, 40, 121 (1970).

Clearly, the endothelial cell plays a key role in the etiology of blood vessel dysfunction. It is anticipated that restoration of intact endothelium immediately following injury might reduce or alter the events occurring immediately after injury. Therefore, it is an object of this invention to provide a method for reendothelializing the linings of vascular passages which have been substantially denuded of endothelial cells.

Recent years have seen refinements made in the isolation of endothelial cells (EC) and their growth in culture. The addition of endothelial cell growth factor (ECFG) and heparin to culture medium has allowed human adult large vessel EC to remain in culture for greater than 50 population doublings. Jaffe, E. A. et al., *J. Clin. Invest.*, 52:2745 (1973); Maciag, T., et al., *J. Cell Biol.*, 91:420 (1981); Thornton, S. C. et al., *Science*, 222:623–624 (1983); Jarrell, B. E., et al., *J. Vasc. Surg.*, 1:757–764 (1984). Human microvessel EC have also been routinely isolated in large quantities using collagenase digestion and Percoll gradient purification followed by long term cultivation in heparin - ECFG supplemented medium. Jarrell, B. E. et al., *Surgery*, Vol. 100, No. 2, pp. 392–399 (August 1986).

These advances in EC isolation and culture have been used to better understand the interactions between these EC and prosthetic vascular grafts. Watkins, M. T. et al., *J. Surg. Res.*, 36:588–596 (1984); Williams, S. K. et al., *J. Surg. Res.*, 38:618–629 (1985); Baker, K. S. et al., *Am. J. Surg.*, 150:197–200 (1985). In these studies it has been noted that human EC possess the ability to firmly adhere to both plasma coated surfaces and human amnion type IV/V collagen after a ten to thirty minute incubation period. Jarrell, B. E. et al., *Ann. Surg.*, Vol. 203, No. 6, pp. 671–678 (June 1986). Another observation was that freshly isolated human microvessel EC obtained from fat tissue also possessed this property and could be isolated in quantities of $10^6$ EC per gram of fat. Radomski, J., et al., *J. Surg. Res.*, 42, 133–140 (1987);

Jarrell, B. E. et al., *Surgery*, Vol. 100, No. 2, pp. 392-399 (August 1986).

At least one study has examined the utility of treating the neointimal hyperplasia developed after endarterectomy of a normal artery by endothelial cell sodding. Bush, Jr., Harry L., Jakubowski, Joseph A., Sentissi, Joanna M., Curl, Richard G., Hayes, John A., and Deykin, Daniel, "Neointimal Hyperplasia Occurring After Carotid Endarterectomy in a Canine Model: Effect of Endothelial Cell Seeding vs. Perioperative Aspirin, Journal of Vascular Surgery, Vol. 3, No. 1, pp. 118-125 (January 1987). In this study, endothelial cells were harvested from the veins of dogs selected to undergo treatment. The cells were suspended in sterile autogenous serum, and this suspension was injected into the endarterectomized segment of the dog's artery. From this work, the authors concluded that sodding the endarterectomized surface with autogenous endothelial cells did minimize proliferative lesion in the artery.

SUMMARY OF THE INVENTION

This invention relates to a method of reendothelializing the vascular passage of a patient, the lining of which has been substantially denuded of endothelial cells, using that patient's own endothelial cells. In this method, endothelial cells are isolated from the patient's own microvessels, the flow of blood through the patient's damaged vascular passage is interrupted, the endothelial cells isolated from the patient's microvessels are applied to the surface of the denuded portion of the patient's vascular passage in a density sufficient to provide coverage of at least about 50% of said denuded portion, and interruption of blood flow through the vascular passage is maintained for a period of time sufficient to allow the cells to form an attachment to the vascular lining sufficient to withstand the shear created by resumed blood flow through the vascular passage.

DETAILED DESCRIPTION OF THE INVENTION

The patients who may benefit from the method of this invention are those who have been subjected to procedures which damage the endothelial cell linings of the vascular passages, e.g., percutaneous transluminal angioplasty. By substantially denuded of endothelial cells, as that phrase is used herein, we mean a vascular passage the endothelial cell lining of which has been injured or removed to an extent likely to cause adverse side effects to the patient. Such injuries can be classified as level I, II or III injuries, level I injury being one that exposes principally basement membrane, level II injury being one that exposes primarily sub-basement membrane, interstitial collagen and the internal elastic lamina, and a level III injury being one that exposes the deeper layers including the media and smooth muscle cells in areas of internal elastic lamina fracture.

Endothelial cells for use in the method of this invention are preferably obtained from the patient undergoing the vascular treatment; however, it should be possible to obtain human perinephric fat from brain-dead but heart-beating cadaver donors or from donors other than the patient during the donor's surgery. Microvascular endothelial cells, that is, cells which are derived from capillaries, arterioles and venules, will function suitably in place of large vessel cells even though there are morphological and functional differences between large vessel endothelial cells and microvascular endothelial cells in their native tissues. Microvascular endothelial cells are present in an abundant supply in body tissue, and are therefore the preferred source of endothelial cells for use in this invention. Although endothelial cells may be isolated from tissues such as brain, lung, retina, adrenal glands, liver and muscle tissue, the use of fat tissue as the source for the cells is preferred due to its abundance and availability, and due to the fact that its removal should not adversely affect the patient being treated.

To obtain microvascular endothelial cells from the patient, the source tissue, such as fat tissue, is removed from the patient after sterile conditions have been established. Microvascular endothelial cells in that fat tissue are then quickly separated from their related tissue by enzymatic digestion and centrifugation and may be used to treat the surface of the damaged vascular linings of the patient during the latter stages of the same operation. This procedure obviates any need to culture adult endothelial cells to increase their numbers, and permits a patient to receive treatment with his own fresh, "healthy" endothelial cells.

The procedure useful for isolating large quantities of endothelial cells without the need for tissue culturing may be readily performed in an operating room and is described in its preferred embodiment in greater detail as follows. The fat tissue retrieved from the patient or donated from another source is immediately transferred to ice cold buffered saline (pH 7.4) wherein the buffering agent is preferably a phosphate, i.e., a phosphate buffered saline (PBS). The tissue is minced with fine scissors and the buffer decanted. Alternatively, fat tissue obtained by liposuction may be used as the source of endothelial cells. The proteolytic enzyme collagenase, containing caseanase and trypsin, is added to the tissue and incubated at 37° C. until the tissue mass disperses. This digestion occurs within thirty minutes and generally should occur in less than twenty minutes. The digest is transferred to a sterile test tube and centrifuged at low speed ($700 \times g$) in a table top centrifuge for five minutes at room temperature. The pellet of cells thus formed consists of greater than ninety-five percent (95%) endothelial cells. These endothelial cells are described herein as microvascular endothelial cells since they originate from the arterioles, capillaries and venules, all elements of the microvasculature. This microvascular endothelial cell pellet is washed one time by centrifugation with a buffer and can be used directly without further purification for application to the injured vascular lining of the patient. Suitable buffers include buffered saline such as PBS as well as intravenous infusion solutions and peritoneal dialysis solutions.

Alternatively, the microvascular endothelial cells may be further purified by centrifuging the cells with a continuous gradient. This gradient can be formed from a number of large molecular weight solutes, including albumin, dextran, or commercially available density gradient materials, such as Percoll (Pharmacia Inc., Piscataway, N.J.) or Nycodenz (Nyegaard and Company, Norway). Gradient centrifugation is used to remove red cells, white cells and smooth muscle cells. A forty-five percent (45%) solution of Percoll has routinely been used in the studies reported herein. Cells are layered on the surface of the Percoll solution and centrifuged at $13,000 \times g$ for twenty minutes. Alternatively, cells are layered on a preformed Percoll gradient and centrifuged at $400 \times g$ for five minutes at room temperature. A thick band of endothelial cells results at the upper end of the gradient. These cells are removed with a pipette and washed one time by centrifugation with phosphate-buffered saline.

The endothelial cells isolated as described above may be used directly to treat the injured vascular lining of the patient. They may be mixed with blood or plasma and used to seed the surface of the patient's vascular lining or may be mixed with a non-clotting medium such as a buffered saline and used to sod the surface. The term "seeding" as it is used herein refers to the procedure which entails mixing cells with a matrix followed by placement of that mixture onto the surface to be seeded, e.g., the vascular lining. The matrix may be any gel or clot-forming substance, such as blood or plasma, that may be used as a vehicle in which to suspend and trap the cells. This endothelial cell matrix mixture adheres to the surface and gels, "trapping" the cells within the matrix until they are able to multiply and grow out over the surface. The term "sodding", on the other hand, is used herein to refer to the procedure which entails mixing cells in a simple medium such as a buffer solution that does not gel under the ambient conditions of the sodding procedure (e.g., a temperature of from about body temperature to about 37° C.) and applying that mixture to cover a surface. In the sodding process, cells approach the surface to be treated due to gravity and attach directly to the surface, rather than being "trapped" within a portion of the mixture as in the seeding process.

In a preferred embodiment, the cells are pelletized by centrifugation (200×g) and the pellet is then resuspended with protein-containing buffer solution. This resuspension should be performed at a ratio of approximately 1:5 to 1:15 or, preferably about 1:10 volumes of packed microvascular endothelial cells to buffer solution. This resuspension may then be used to sod the lining of the injured vascular passageway. Prior to sodding, certain agents may be added to the suspension in an effort to aid cell adhesion and spreading, including fibronectin, platelet poor plasma, albumin, Dextran 40 or Dextran 70, endothelial cell growth factor and heparin sulfate.

The goal in this procedure, of course, is to create a confluent layer of endothelial cells on the vascular surface, or to restore the vascular surface to its pre-injury, "healthy" state. To achieve this goal, the initial adherence of cells to the vascular lining surface should preferably be sufficient to provide at least about fifty percent (50%) initial surface coverage. Application at fifty percent (50%) confluence requires the cells to duplicate one time to create a confluent cell layer. Since, as discussed below, it will be necessary to restrict the flow of blood through the vascular passageway during the seeding or sodding process, since such flow restriction should be maintained for as short a time as possible for the benefit of the patient, and since resumed blood flow through the passageway may hinder cell duplication, it is obviously desirable to apply as many endothelial cells to the vascular lining surface as possible. Most preferably, the cells are seeded or sodded onto the vascular lining surface at a density equivalent to confluence, i.e., greater than about $10^5$ cells per $cm^2$ surface area. It is necessary to interrupt or reduce the flow of blood through the vascular passageway during the time of seeding or sodding for a period of time sufficient to permit adhesion of the cells to the lining of that passageway. More preferably, flow is interrupted or reduced for a period of time sufficient for adhesion of a confluent monolayer of cells. For certain arteries, it may be necessary to use a temporary shunt around the affected portion to sufficiently reduce blood flow. In other situations, the artery may simply be clamped or constricted upstream to accomplish the necessary flow reduction. It is preferable, especially in the sodding procedure, to apply pressure to force the cells against the vessel wall. It is believed that the optimal temperature for inducing attachment of the cells to the vessel wall is about 37° C. Once the endothelial cells have established an attachment sufficient to withstand the shear created by the blood flow through the vascular passageway, flow may be reestablished therethrough, whereupon the previously denuded portion of the passageway will be protected by a "natural" antithrombogenic surface.

Studies on human basement membrane surfaces obtained from amnion have suggested that type IV/V collagen exhibits properties which support rapid adherence and spreading of endothelial cells after sodding. Conversely, human plasma derived clot and human type I/III interstitial collagen have been found to support less rapid cell spreading when examined under similar conditions. An injured vessel will most likely expose collagen I/III smooth muscle cells or become coated with plasma proteins, providing a suboptimal surface for endothelial cell attachment and spreading. Pre-treatment of the residual injured vessel wall may enhance adherence and spreading qualities and allow a more satisfactory surface to form. Thus, the vessel wall may be pretreated with one or more of the following:

fibronectin
laminin
plasma, prepared with EDTA and clotted onto surface
solubilized collagen IV/V
platelets
red blood cells
Dextran 40 or Dextran 70
heparin sulfate
endothelial cell growth factor
serum
serum albumin
thrombospondin
heparan
heparan sulfate

What is claimed is:

1. A method of reendothelializing the vascular passage of a patient, the lining of which has been substantially denuded of endothelial cells, comprising
   (a) interrupting the flow of blood through said vascular passage,
   (b) applying to said denuded vascular lining uncultured endothelial cells retrieved from the microvessels of said patient in a density sufficient to provide coverage of at least about 50% of said denuded portion; and
   (c) maintaining the interruption of blood flow through said vascular passage for a period of time sufficient to allow 5 said applied cells to form an attachment to said vascular lining sufficient to withstand the shear created by resumed blood flow through said vascular passage.

2. The method of claim 1 where said endothelial cells are applied in a density of at least about $1 \times 10^5$ cells per $cm^2$ of seeded surface.

3. The method of claim 1 where said endothelial cells are applied in a density sufficient to form a confluent layer of said cells on said vascular lining.

4. The method of claim 1 where said endothelial cells are applied to said vascular passage in a suspension of blood or plasma.

5. The method of claim 2 where said endothelial cells are applied to said vascular passage in a suspension of blood or plasma.

6. The method of claim 3 where said endothelial cells are applied to said vascular passage in a suspension of blood or plasma.

7. The method of claim 1 where said endothelial cells are applied to said vascular passage in a suspension of a non-gel-forming buffer solution.

8. The method of claim 2 where said endothelial cells are applied to said vascular passage in a suspension of a non-gel-forming buffer solution.

9. The method of claim 3 where said endothelial cells are applied to said vascular passage in a suspension of a non-gel-forming buffer solution.

10. The method of claim 1 where said endothelial cells are derived from the fat tissues of the patient.

11. The method of claim 4 where said endothelial cells are derived from the fat tissues of the patient.

12. The method of claim 7 where said endothelial cells are derived from the fat tissues of the patient.

13. The method of claim 1 where said endothelial cells are retrieved from said patient and applied to said patient's vascular lining during the sam operative procedure.

* * * * *

UNITED STATES PATENT AND TRADEMARK OFFICE
CERTIFICATE OF CORRECTION

PATENT NO. : 4,883,755
DATED : November 28, 1989
INVENTOR(S) : Carabasi et al.

It is certified that error appears in the above-identified patent and that said Letters Patent is hereby corrected as shown below:

Cover page, Col. 2, line 11, in the Publications delete "Fascular" and insert -- Vascular --.

Col. 3, line 45, please add quotes around the phrase -- "substantially denuded of endothelial cells" --.

Col. 5, line 61 delete "105" and insert -- $10^5$ --.

Col. 6, line 59, delete the number "5" between "allow" and "said".

Col. 8, line 15, delete "sam" and insert -- same --.

Signed and Sealed this

Twenty-first Day of May, 1991

Attest:

HARRY F. MANBECK, JR.

*Attesting Officer*     *Commissioner of Patents and Trademarks*